(12) United States Patent
Richardson

(10) Patent No.: US 7,976,460 B2
(45) Date of Patent: Jul. 12, 2011

(54) CONE TIP BILIARY CATHETER AND METHOD OF USE

(75) Inventor: Kevin Richardson, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1990 days.

(21) Appl. No.: 10/830,928

(22) Filed: Apr. 22, 2004

(65) Prior Publication Data

US 2004/0199050 A1 Oct. 7, 2004

Related U.S. Application Data

(63) Continuation of application No. 10/047,482, filed on Oct. 23, 2001, now abandoned.

(51) Int. Cl.
*A61B 1/00* (2006.01)
*A61M 31/00* (2006.01)
*A61M 1/00* (2006.01)
*A61M 29/00* (2006.01)

(52) U.S. Cl. ..... 600/116; 604/540; 604/514; 604/96.01; 604/104

(58) Field of Classification Search ............... 604/544, 604/540, 101.01, 101.05, 103.06, 103.07, 604/103.08, 93.01, 104–109, 500, 514, 96.01–103; 600/31, 116; 606/191, 200
See application file for complete search history.

(56) References Cited

U.S. PATENT DOCUMENTS

| 5,275,610 | A | 1/1994 | Eberbach |
| 5,320,602 | A | 6/1994 | Karpiel |
| 5,397,302 | A | 3/1995 | Weaver et al. |
| 5,800,394 | A | 9/1998 | Yoon et al. |
| 6,692,484 | B1 * | 2/2004 | Karpiel et al. ............ 604/544 |
| 2001/0044595 | A1 * | 11/2001 | Reydel et al. ............ 604/98.02 |
| 2002/0183826 | A1 | 12/2002 | Dorn et al. |
| 2003/0009130 | A1 | 1/2003 | Stecker et al. |

OTHER PUBLICATIONS

Internet Article: ERCP, (NIDDK) site unknown, dated on or before Oct. 23, 2001, 3 sheets.
Internet Article: "ERCP and Stent Placement," www.gihealth.com/TREC2/scopephotos/ercp_stent, Jul. 31, 2000, 2 sheets.
Internet Article: "ERCP," www.gihealth.com/TREC2/articles/ercp, Jul. 31, 2000, 3 sheets.
Internet Article: "ERCP," site unknown, dated on or before Oct. 23, 2001, 2 sheets.
Siegel, Jerome H., M.D. et al., "Two New Methods For Selective Bile Duct Cannulation and Sphincterotomy", *Gastrointestinal Endoscopy*, vol. 33, No. 6, Dec. 1987, pp. 438-440.

* cited by examiner

*Primary Examiner* — Matthew F Desanto
(74) *Attorney, Agent, or Firm* — Seager, Tufte & Wickhem, LLC

(57) ABSTRACT

A catheter system is provided that permits easy cannulation and radiological examination of the biliary and pancreatic ducts during an Endoscopic Retrograde Cholangiopancreatograhy (ERCP) procedure. The system of biliary catheters provides for a method of gaining access to the biliary tree, particularly when the contralateral wall or septum of the biliary tree interferes with access to the biliary tree. This anatomical interference is remedied using a pulling biliary catheter that withdraws the papilla of Vater away from the contralateral wall or septum by pulling proximally upon a chute expanded within the papilla of Vater. The enlarged opening then permits additional medical devices to be advanced through the pulling biliary catheter into the desired duct requiring the ERCP procedure.

23 Claims, 6 Drawing Sheets

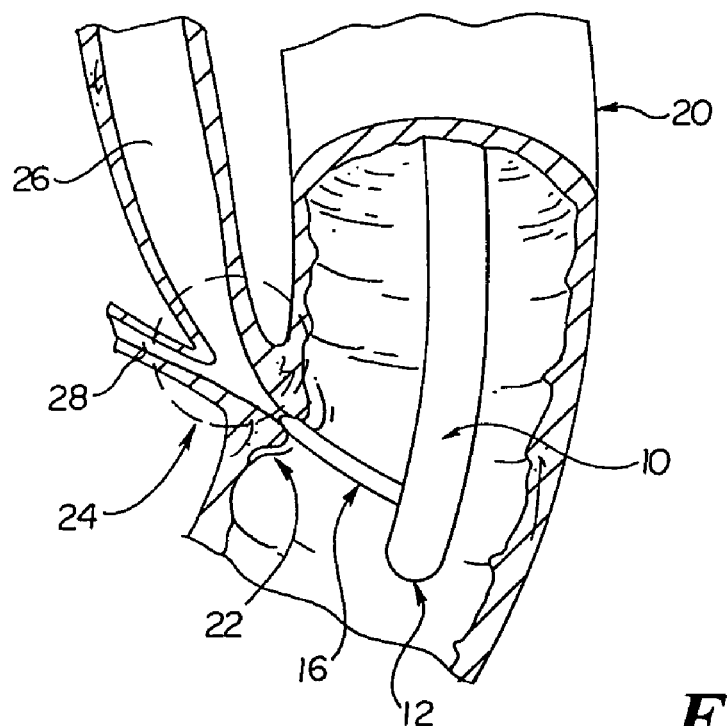
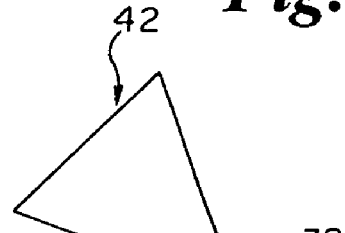
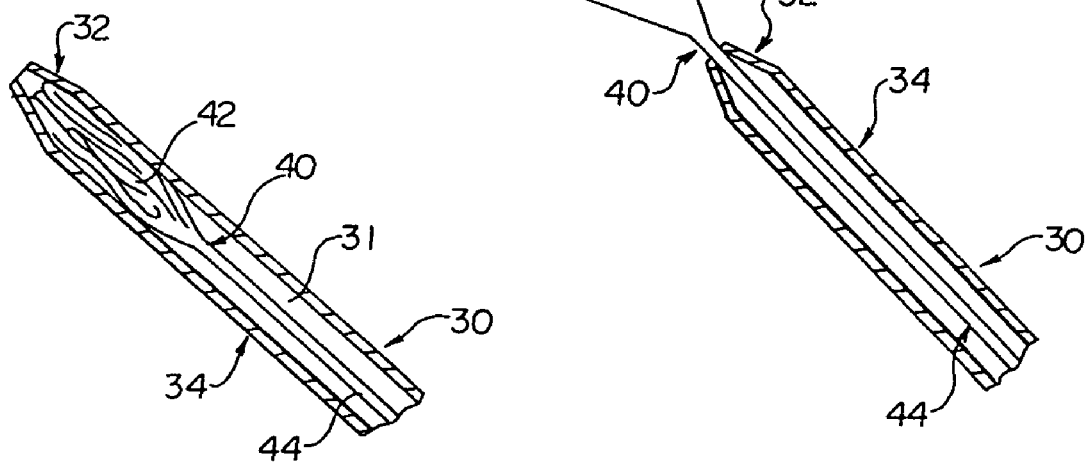

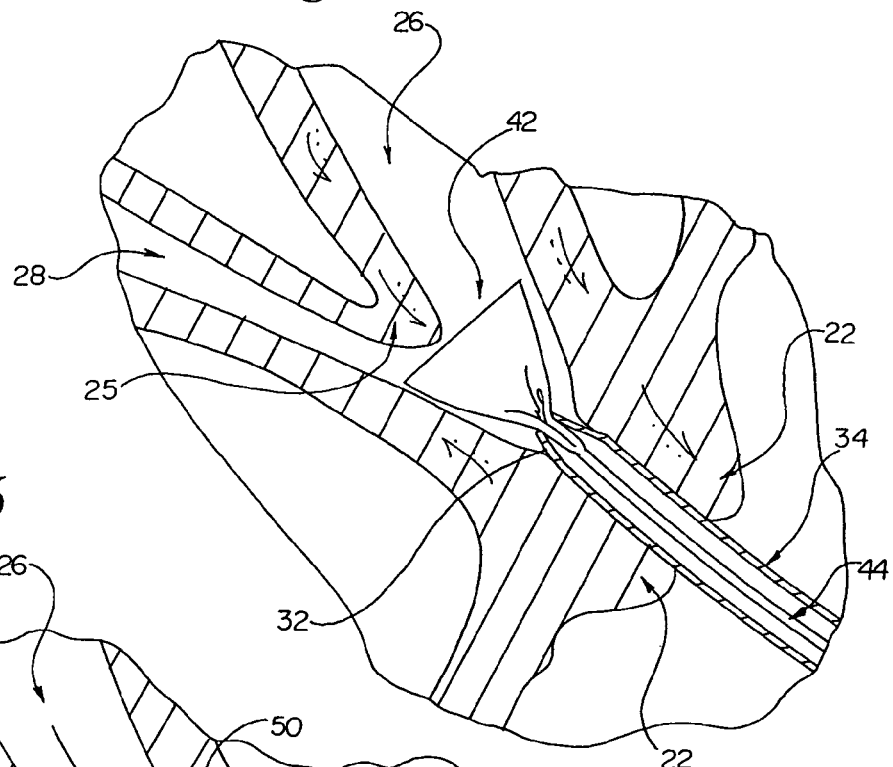
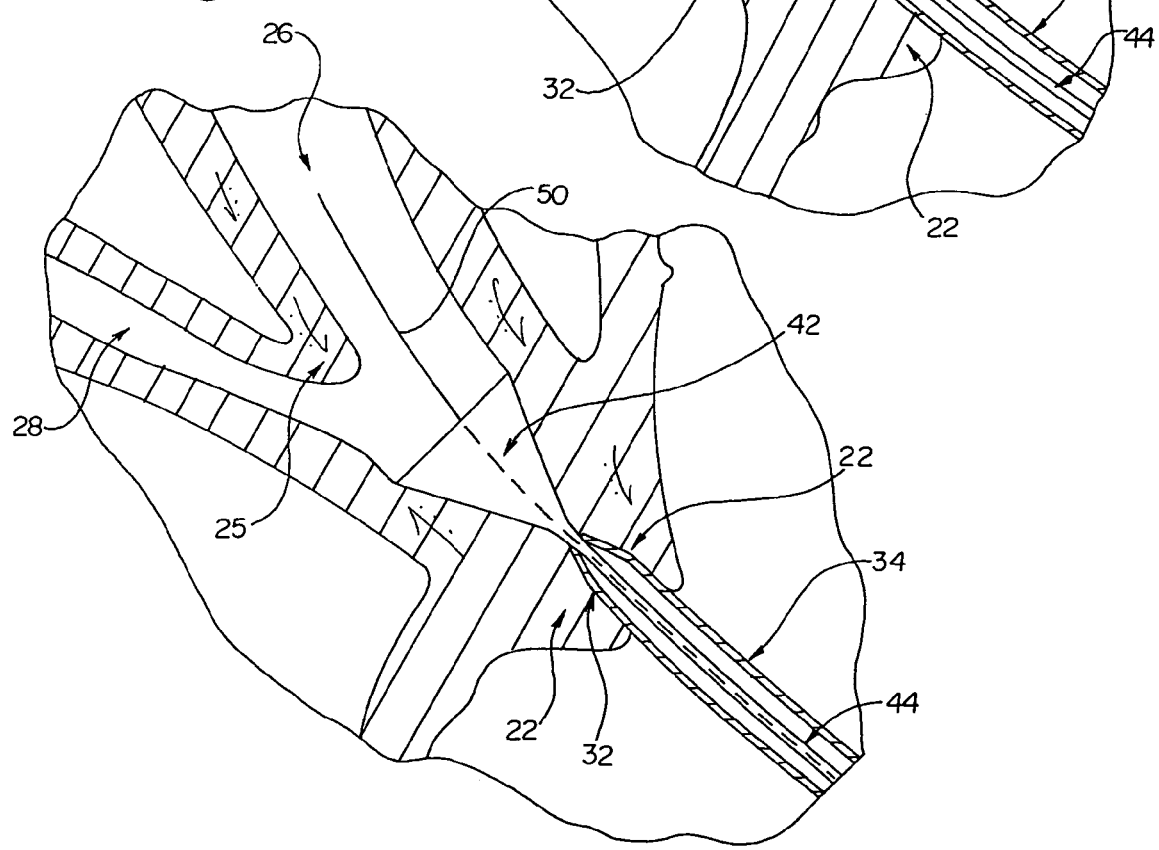

CONE TIP BILIARY CATHETER AND METHOD OF USE

This application is a continuation of application Ser. No. 10/047,482, filed Oct. 23, 2001 now abandoned.

FIELD OF THE INVENTION

The present invention relates generally to a biliary catheter for use in Endoscopic Retrograde Cholangiopancreatograhy (ERCP) procedures within the human anatomy, and methods of using the same. The present invention specifically includes a biliary catheter having a distal tip that facilitates cannulation through the papilla of Vater.

DESCRIPTION OF THE PRIOR ART

Endoscopic Retrograde Cholangiopancreatography (ERCP) is an endoscopic technique that involves the placement of a side-viewing instrument (generally either an endoscope or duodenoscope) within the descending duodenum. The procedure eliminates the need for invasive surgical procedures for identifying biliary stones and other obstruction or abnormalities of the biliary and pancreatic ducts.

The number of ERCP procedures performed each year is on the rise. Endoscopic procedures allow physicians to treat abnormal pathologies within the alimentary canal system and biliary tree (including the biliary, hepatic, and pancreatic ducts) using minimally invasive techniques. An endoscope provides the initial access and direct visualization of the general area of treatment. The endoscope, however, is limited to certain locations within the alimentary system on account of its size. Once an endoscope is positioned in the general area of interest, the endoscope is used as a conduit for other medical devices. It is these additional medical devices, which pass through the endoscope, which are used to navigate and treat the abnormal pathologies within the desired duct. These medical devices are subsequently navigated using a catheter in conjunction with fluoroscopy and guidewires.

In an ERCP procedure, the patient will generally lie on their side on an examining table. The patient will then be given medication to help numb the back of the patient's throat, and a sedative to help the patient relax during the examination. The patient then swallows the endoscope. The thin, flexible endoscope is passed carefully through the alimentary canal of the patient. The physician guides the endoscope through the patient's esophagus, stomach, and the first part of the small intestine known as the duodenum. Because of the endoscope's relatively small diameter, most patients can tolerate the unusualness of having the endoscope advanced through the opening of their mouth.

The physician stops the advancement of the endoscope when the endoscope reaches the junction where the ducts of the biliary tree and pancreas open into the duodenum. This location is called the papilla of Vater, or also commonly referred to as the ampulla of Vater. The papilla of Vater is a small mound of tissue looking and acting similarly to a nipple. The papilla of Vater emits a substance known as bile into the small intestine. Bile is a combination of chemicals made in the liver and is necessary in the act of digestion. Bile is stored and concentrated in the gallbladder between meals. When digestive indicators stimulate the gallbladder, however, the gallbladder squeezes the bile through the common bile duct and subsequently through the papilla of Vater.

The patient will be instructed (or manually maneuvered) to lie flat on their stomach once the endoscope reaches the papilla of Vater. For visualization or treatment within the biliary tree, the distal end of the endoscope is positioned proximate the papilla of Vater. A biliary catheter is then advanced through the endoscope until the distal tip of the biliary catheter emerges from the opening at the endoscope's distal end. The distal end of the biliary catheter is guided through the endoscope's orifice to the papilla of Vater (located between the sphincter of oddi) leading to the common bile duct and the pancreatic duct. Known methods and devices for using biliary catheters for accessing the biliary tree for ERCP procedures are disclosed in Weaver et al., U.S. Pat. No. 5,397,302 and Karpiel, U.S. Pat. No. 5,320,602, the disclosures of which are herein incorporated by reference.

Cannulation of the papilla of Vater is often a daunting task for the physician. The physician must gently press the tip of the biliary catheter, or guidewire, into and through the opening of the papilla of Vater. The physician will advance the biliary catheter until resistance is met, at which time, the physician may opt to probe with a guidewire to aid in advancement. Progress is made, if any, in small increments with firm but gentle advances of both the guidewire and biliary catheter.

Sometimes, however, despite the best efforts of the physician, cannulation of the papilla of Vater will not occur through traditional "push-pull" techniques. A physician, in these cases, may probe the papilla of Vater for up to thirty minutes with little success, denying any access to either of the pancreatico-biliary ducts. Prolonged probing causes inflammation of the papilla. The physician, aware that the papillary tissue is extremely delicate, is wary of prolonged repeated attempts at cannulation of the papilla of Vater. Each attempt at cannulation increases trauma to the surrounding tissue, and subsequently, increases the discomfort experienced by the patient.

In order to increase the success of cannulation, innovations in ERCP have focused primarily on the shape of the distal tip of biliary catheters. Cannulation devices come in all types, shapes and sizes. The current trend, however, includes the use of a small tipped biliary catheter having a gradual taper toward the catheter's distal-most end. It is generally believed that using a tapered tip will allow the distal region of the biliary catheter to easily slide through the folds of the papillary tissue. This current philosophy of innovation is susceptible to one primary disadvantage. No matter what type, shape or size biliary catheter a physician uses, the physician must still apply a forward pressure to cannulate the papilla of Vater. Such forward pressure, as described above, causes trauma and subsequent inflammation to the surrounding sensitive papillary tissue.

A second disadvantage of focusing primarily on the shape of the biliary catheter is that regardless of the shape, a biliary catheter cannot be advanced through a papilla of Vater, whose opening is positioned against the contralateral wall, or septum, separating the pancreatico-biliary ducts. This anatomical positioning generally prevents access to either the common bile or pancreatic ducts.

A physician may attempt to lift the papilla away from the septum wall of the pancreatico-biliary ducts if access through the papilla is not immediately achieved due to the positioning of the septum wall. Some physicians will use this technique after repeated attempts at cannulation, or when cannulation is only possible into the wrong duct, the septum having closed off the desired duct. The procedure generally requires the use of a sphincterotome, or a similar device, to gently lift and pull the papilla tissue. After sufficient pulling, the papilla opening will ideally separate from the septum providing a physician access to the appropriate duct system. As described earlier, however, the papillary tissue is very delicate and prone to inflammation. Grabbing and pulling on this tissue inevitably leads to undesirable trauma.

SUMMARY OF THE INVENTION

The biliary catheters of the present invention permit easy cannulation and radiological examination of the biliary and pancreatic ducts of a patient during ERCP procedures. The present invention overcomes the disadvantages of the prior art by modifying the catheter design and method currently used for cannulation of the papilla of Vater.

Most catheter manufacturers have adopted catheter designs specifically for "push-pull" cannulation. As a result, most biliary catheters are designed with thin, tapered distal ends. The present invention utilizes aspects of these design innovations, but not for pushing or advancing the catheter. In a preferred embodiment, the present invention utilizes the tapered distal most end of a guide biliary catheter to engage and enter, but generally not to probe past, the orifice of the papilla of Vater. The guide biliary catheter gains entry to the opening of the papilla of Vater, is advanced slightly within the opening, and is generally refrained from any further advancement. In effect, the guide biliary catheter removes the "push" from "push-pull" cannulation.

The present invention also modifies the "pull" technique by using a biliary catheter that does not pull on the outside tissue of the papilla of Vater, but rather pulls from within the papilla of Vater. In a preferred embodiment of the present invention, a pulling biliary catheter deploys a cone-shaped chute within the orifice of the papilla of Vater. The resulting chute possesses a circumferential diameter greater than the orifice of the papilla of Vater. When a physician gently pulls back upon the pulling biliary catheter, the chute gently moves tissue away from the contralateral wall, thereby further cannulating the papilla of Vater. A physician may then easily access either of the pancreatico-biliary ducts once the tissue is moved away from the contralateral wall. A lumen running through the chute allows subsequent guidewires and catheters to selectively gain access to these ducts for further exploration and treatment.

In another preferred embodiment, a biliary catheter having a balloon disposed either near or on the distal tip of the catheter is utilized. The catheter deploys the balloon within the orifice of the papilla of Vater. The balloon is deployed to a diameter that is greater than the orifice of the papilla of Vater. A physician may then pull back gently on the balloon catheter to move tissue away from the contralateral wall. A lumen running through the balloon catheter allows subsequent guidewires and catheters to selectively gain access to the pancreatico-biliary ducts for further exploration and treatment.

BRIEF DESCRIPTION OF THE DRAWINGS

FIG. 1 illustrates the advancement of an endoscope through the alimentary canal to a position adjacent the papilla of Vater;

FIG. 2 is a partial cross-sectional view of the distal end of a guide biliary catheter having a pulling biliary catheter loaded therein;

FIG. 3 is a partial cross-sectional view of a guide biliary catheter and a pulling biliary catheter wherein the chute of the of the pulling biliary catheter is deployed at the catheter's distal-most end;

FIG. 5 illustrates the introduction of the pulling biliary catheter within the orifice of the papilla of Vater and the initial deployment of the pulling biliary catheter's chute;

FIG. 6 illustrates the withdrawal of the papilla of Vater from the contralateral wall using the deployed chute of the pulling biliary catheter;

DETAILED DESCRIPTION OF THE PREFERRED EMBODIMENTS

Figure 4:
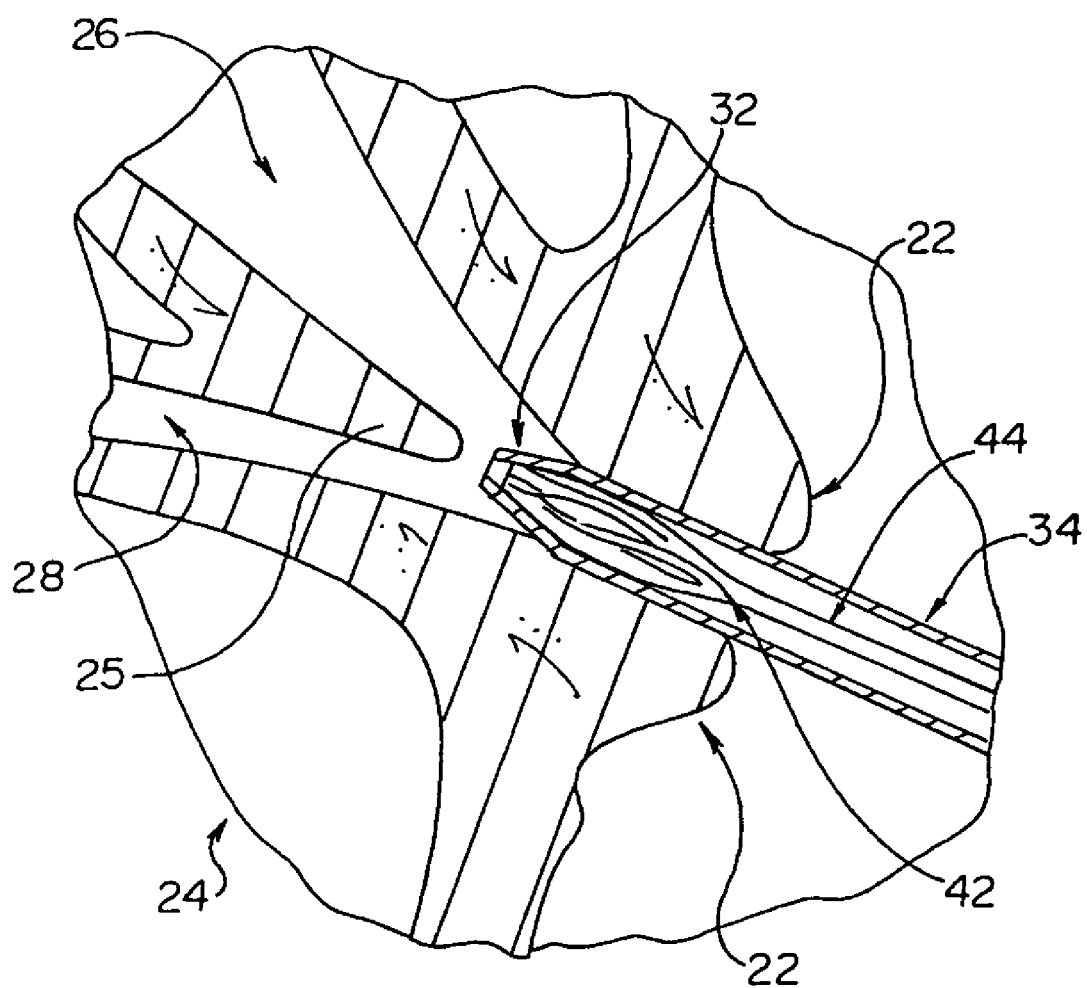
FIG. 4 is a partial cross-sectional view of the engaging distal tip of the guide biliary catheter gaining access within the opening of the papilla of Vater.

The following detailed description should be read with reference to the drawings, in which like elements in different drawings are numbered identically. The drawings, which are not necessarily to scale, depict selected embodiments and are not intended to limit the scope of the invention. Examples of constructions, materials, dimensions, and manufacturing processes are provided for selected elements. Those skilled in the art will recognize that many of the examples provided have suitable alternatives that may be utilized.

Refer now to the drawings, wherein FIG. 1 shows the advancement of endoscope 10 through the alimentary canal 20 to a position adjacent the papilla of Vater 22. Endoscope 10 provides the initial access and direct visualization of the general area of treatment. The thin, flexible endoscope 10 has a proximal end (not shown), a distal end 12, and at least one lumen extending the length thereof.

The proximal end possesses a hub assembly allowing additional medical instruments access to the endoscope's inner lumen or lumens, and a means for attachment thereto. In one embodiment, the hub assembly contains a series of ports. These ports generally have a luer lock fitting located on the distal-most end of each individual port. When utilizing an endoscope possessing such port fittings, additional medical instruments may be threaded through port openings and subsequently secured to endoscope 10 by affixing the medical instrument to the luer lock provided on that port.

Endoscope 10 is passed carefully through the alimentary canal 20 of the patient. The physician guides endoscope 10 through the patient's esophagus, stomach, and stops when distal end 12 of endoscope 10 reaches the duodenum. More specifically, the physician stops the advancement of endoscope 10 when the endoscope reaches the papilla of Vater 22, where the ducts of the biliary tree and pancreas open into the duodenum.

The distal end 12 of endoscope 10 generally possesses a side opening in fluid communication with the lumen. Additional medical devices emerge from endoscope 10 from this side opening. It is these additional medical devices, which pass through endoscope 10, which are used to navigate and treat the abnormal pathologies within the desired duct. In particular, a biliary catheter 16 is advanced through endoscope 10 until the distal tip of biliary catheter 16 emerges from the endoscope 10 side opening and is advanced to the papilla of Vater 22 leading to the common bile duct 26 and the pancreatic duct 28. A guidewire (not shown) may be used in conjunction with biliary catheter 16 to aid in accessing a desired location within the biliary tree 24. The guidewire is inserted in an opening at a proximal end of biliary catheter 16 and guided through the catheter lumen until it emerges from the distal end of the biliary catheter. Biliary catheter 16 is then advanced over the guidewire until the distal end of the catheter is positioned in the biliary tree 24 at the desired location.

Biliary catheter 16 is now in a position for delivery of contrast media within the desired duct. Contrast media allows for fluoroscopic visualization of anatomical detail within the biliary tree 24. Through endoscope 10, and subsequently biliary catheter 16, the physician will inject a dye into the biliary tree 24. A radiographer will begin taking fluoroscopic images as soon as the dye is injected.

Contrast media visualization by the radiographer may reveal abnormalities within the common bile duct 26 or pancreatic duct 28 that require treatment. When the diagnosis necessitates, the physician inserts the appropriate medical instruments through endoscope 10 to access the targeted areas. For example, if the examination shows a gallstone or narrowing of the ducts, the physician may insert medical instruments through endoscope 10 to remove or work around the obstruction.

FIG. 2 shows a guide biliary catheter 30 having an engaging distal tip 32 for abutment with the papilla of Vater 22. In a preferred embodiment, the guide biliary catheter 30 of the present invention comprises a cannula 34, or tube having a proximal end and a distal end. The proximal end of guide biliary catheter 30 possesses a hub assembly. The hub assembly permits guide biliary catheter 30 to attach to endoscope 10, as well as permitting additional medical devices to attach thereto.

Cannula 34 comprises of at least one lumen running the length of the catheter. In one embodiment, cannula 34 is approximately 200 centimeters in length. The length of cannula 34, however, may be varied to complement the body type of the patient. The lumen size chosen by the physician may possess a diameter of such area permitting the passage of at least two additional medical instruments and fluids therethrough.

The distal portion of guide biliary catheter 30 has a gradually tapering distal-most tip 32. The distal taper generally begins approximately 0.10 to 5.0 centimeters from the distal-most tip 32. In one embodiment, the taper begins 0.5 centimeters from the distal-most tip 32 of guide biliary catheter 30. Tapering the distal-most tip 32 greatly reduces the catheter's initial profile. A reduced profile increases the probability of initially breaching and cannulating smaller openings such as the orifice leading through the papilla of Vater 22.

Because distal tip 32 is tapered, the diameter of the taper increases as the catheter is advanced proximally along its distal portion. The degree of tapering on distal-most tip 32 directly relates to the amount of dilation desired. A long and shallow tapered distal tip 32 allows for a smooth and gradual dilation, however, it also requires that distal tip 32 be advanced over a longer distance in order to obtain the desired dilation. In contrast, a shorter and steeper tapering requires less advancement, yet makes dilation more immediate, and possibly more difficult.

FIG. 2 further shows a pulling biliary catheter 40 advanced to the distal tip 32 of guide biliary catheter 30. Similar to guide biliary catheter 30, pulling biliary catheter 40 comprises a proximal end, a distal end, and a cannula 44 having at least one lumen running the length therebetween. The proximal end of pulling biliary catheter 40 possesses a hub assembly that permits pulling biliary catheter 40 to attach to guide biliary catheter 30 or endoscope 10, as well as permitting additional medical devices to attach thereto.

The cannula 44 of pulling biliary catheter 40 is generally smaller, and longer than that of guiding biliary catheter 30. The size difference permits pulling biliary catheter 40 to be inserted within a lumen 31 of guide biliary catheter 30. Likewise, since pulling biliary catheter 40 must be advanced farther into a patient's body during an ERCP procedure, pulling biliary catheter 40 is generally longer than guiding biliary catheter 30.

FIG. 3 shows a perspective view of a pulling biliary catheter 40 having a chute 42 deployed at the catheter's distal-most end. Unlike the distal end 32 of guide biliary catheter 30, pulling biliary catheter 40 possesses a distal most tip that forms a chute 42. When chute 42 is deployed, the chute 42 expands radially to a circumference greater than the circumference of cannula 44. When chute 42 is not deployed, chute 42 is packaged or folded in a profile that mimics the dimensions of cannula 44 positioned proximate the chute 42, as shown in detail in FIG. 2.

Chute 42 preferably includes radiopaque markers in order to determine its location with respect to both guide biliary catheter 30 and the papilla of Vater 22. Radiopacity can be imparted to chute 42 using numerous techniques known in the art.

The deployment of chute 42 can be initiated in any of various ways. In certain designs, deployment of chute 42 may be aided using particular construction materials. For example, construction materials such as polymers enable chute 42 to be self-expanding or self-deploying. Self-expanding chutes, however, require a sleeve or sheath to be positioned over the chute 42 during the pulling biliary catheter 40's advancement. Once positioned, the sleeve or sheath may be removed or retracted allowing chute 42 to expand.

In certain applications, the inner lumen of guide biliary catheter 30 may act as a sheath. When advancing pulling biliary catheter 40 through guide biliary catheter 30, the inner lumen restricts the deployment of the pulling biliary catheter chute 42. As the pulling biliary catheter 40 is advanced through the distal tip 32 of guide biliary catheter 30, the chute 42 begins to deploy. Chute 42 becomes fully deployed when the entire chute section emerges from the distal tip 32 of guide biliary catheter 30. Other means of imparting the chute's deployment action are within the scope of the present invention and will occur to those of ordinary skill in the art.

A preferred embodiment for the shape of chute 42 includes forming a semi-rigid cone when deployed. The semi-rigid cone possesses a distal end circumference larger than the opening of the papilla of Vater 22 when chute 42 is deployed. More specifically, chute 42 forms a truncated cone when deployed. The truncated cone expands radially from the distal end of cannula 44, which forms the base of the cone. The cone forms the distal-most end of the biliary catheter 40. Cone-shaped chute 42 is in fluid communication with the lumen of cannula 44 of pulling biliary catheter 40. In particular, at least one lumen from within cannula 44 extends through the proximal end of chute 42, allowing access to the surrounding environment.

Figure 7:
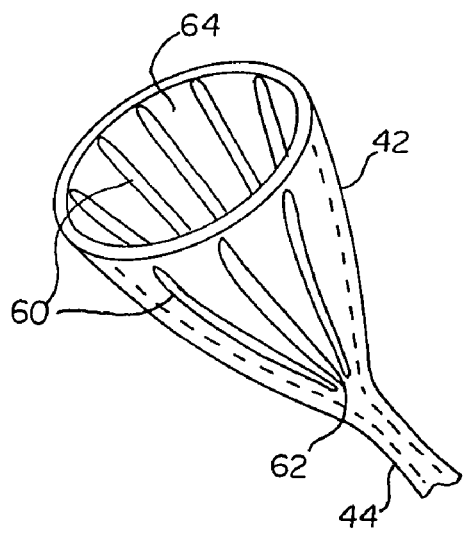
FIG. 7 is a diagrammatic view of a chute incorporating struts.

As depicted in FIG. 7, in one embodiment, chute 42 is constructed from or incorporates a plurality of struts 60. The proximal ends 62 of the struts 60 are adjoined to the distal end of cannula 44. The struts radiate outwardly when fully deployed, forming a uniform circular or oval pattern. Suitable polymeric or metallic materials may be used to form the struts. In a particular embodiment, the struts are made of Nitinol.

Those of ordinary skill in the art are familiar with the superelastic qualities of Nitinol. The use of Nitinol permits the struts to physically alter their shape in response to specific stimuli. In particular, Nitinol struts are capable of expanding or contracting when exposed to temperature fluctuations. In one embodiment, passing an electric current through pulling biliary catheter 40 to the struts in chute 42 would result in a temperature fluctuation sufficient to cause the shape of the Nitinol struts to alter. For example, if the temperature of the Nitinol struts were raised, the struts could expand from a linearly confined configuration to a fully deployed configuration.

Polymeric webbing 64 is generally attached to or spans between the struts. Preferably thin webbing 64 is applied over the outside and ends of the struts. Applying the webbing 64 to the outside and ends of the struts 60 creates a smooth outer surface. A smooth outer surface is preferred in order to reduce trauma caused by physical contact with bodily tissue. Applying webbing 64 over the body of the struts additionally provides a contiguous outer layer between the distal end of cannula 44 and the body of chute 42.

Figure 10:
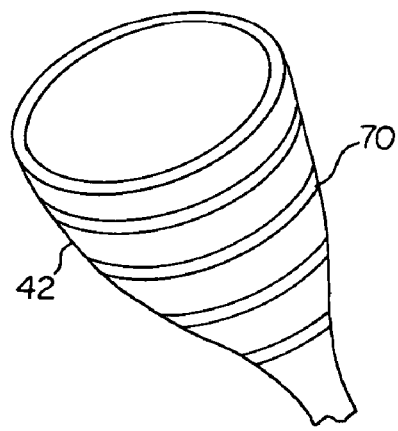
FIG. 10 is a diagrammatic view of a chute incorporating a coil assembly.

In an alternative embodiment, depicted in FIG. 10, chute 42 may be formed from a coil 70 emerging from the distal end of cannula 44. The coil is preferably wire-shaped to easily impart the desired cone shape to chute 42. Various shaped wires, however, may be used to form the coil. As such, the coil may be manufactured as a round wire, a wire ribbon, a cable wire, or a machined hypotube. The wire may be manufactured from stainless steel, tungsten, tantalum, platinum, gold, and the like. Preferably, the wire is manufactured from Nitinol to make use of the superelastic qualities described in detail above.

The wire generally extends from the distal end of cannula 44 in a helical configuration. The windings of the coil increase in size as the windings move distally away from cannula 44. Chute 42 may additionally comprise a series of compressible concentric rings that increase in circumference as the rings move distally away from cannula 44. In preferred embodiments, polymeric webbing encircles the wire windings or concentric rings.

A winding configuration allows the coil to easily compress within a confined environment. As the coil is compressed, the windings slide along one another, increasing the coil's longitudinal profile while decreasing the coil's circumferential profile. When removed from the confined environment, the windings relax forming the pre-confined conical shape.

Figure 9:
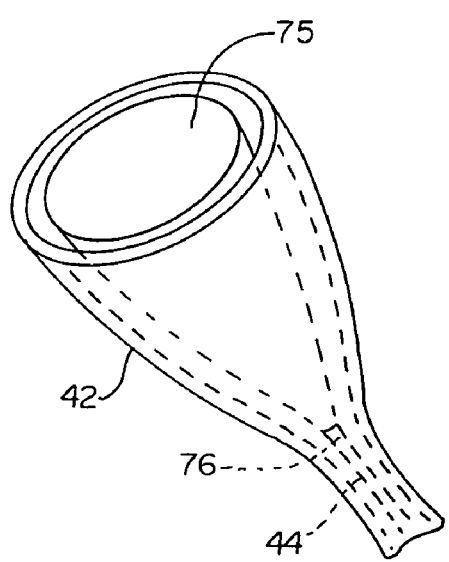
FIG. 9 is a diagrammatic view depicting a semi-rigid polymeric chute and as alternative expanding balloon disposed therein.

In yet another embodiment depicted in FIG. 9, chute 42 may be formed from a semi-rigid polymeric material. In preferred embodiments, the semi-rigid polymeric chute 42 forms a cone, wherein the walls of the cone expand radially outward away from the distal end of cannula 44. The inside of the cone allows fluid communication between the surrounding environment and a lumen within cannula 44.

Semi-rigid polymeric materials are capable of collapsing to a narrow profile without jeopardizing the chute 42 overall integrity. The semi-rigid polymeric material can additionally expand freely to its original configuration when relieved of the stress of a confined environment (e.g., within a sheath, sleeve, or lumen of a larger catheter). Chutes 42 formed from semi-rigid polymeric materials do not require additional support members, such as struts and coils, in order to retain their deployment configuration after being constricted. In certain embodiments, however, these support members may be included to enhance certain performance characteristics of chute 42.

Alternatively, as also depicted in FIG. 9, if the cone 42 is not self-expanding when extended outside the cannula, an inflatable member 75 can be disposed therein. The inflatable member is fluidly connected to an inflation tube 76. When in position, the balloon 75 is inflated at least temporarily to form the cone 42.

Figure 8:
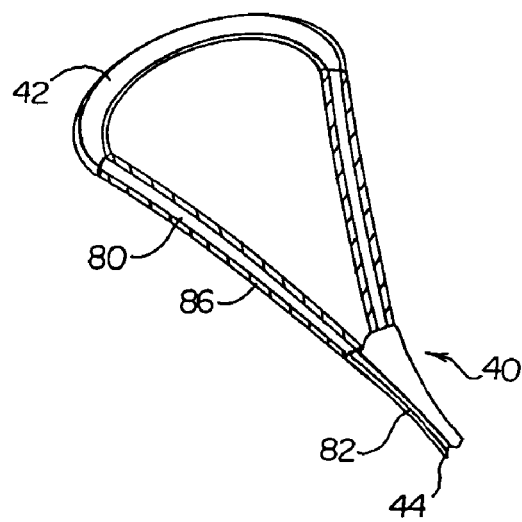
FIG. 8 is a partial cross-sectional view of an inflatable chute.

In an additional embodiment, pulling biliary catheter 40 may possess a chute 42 that forms an inflatable member. This embodiment is depicted in FIG. 8. The inflatable member 80 is in fluid communication with a lumen 82 running within cannula 44, and further exiting through a port on the hub assembly. The inflatable member may be expanded and contracted by adjusting the pressure applied through the above-described lumen. Positive pressure expands the inflatable member, while negative pressure contracts the inflatable member.

An inflatable member 80 generally remains within a contracted configuration after being advanced through the guide biliary catheter 30. Thus, a chute 42 using an inflatable member is generally not self-expanding. Because an inflatable chute 42 is not self-expanding, additional devices such as sheaths and sleeves are not required for the chute's proper deployment. In contrast, the inflatable member chute 42 is inflated by applying positive pressure after being properly positioned within the orifice of the papilla of Vater 22.

When fully expanded, the inflatable member chute 42 is circumferentially larger than the opening of the papilla of Vater 22. The inflatable member chute 42 may take on a variety of shapes when expanded. In general, expanded inflatable members are circular, oval, square, rhombus, diamond, or pyramid in shape, among others.

Inflatable member chute 42 may be contiguous with the distal end of the cannula 44, or polymeric webbing may separate the inflatable member from the cannula 44. Inflatable members that are contiguous with cannula 44 expand uniformly about the cannula's distal end. As such, the walls 86 forming chute 42 are also inflatable. Inflatable walls provide a more rigid and defined chute 42.

The inflatable member may additionally be positioned remotely from the distal end of cannula 44. In this configuration, a lumen is extended from the distal end of cannula 44 to the inflatable member. The inflatable member then acts as the distal end of chute 42. Polymeric webbing is generally used to tether the inflatable member to the distal end of cannula 44. The webbing generally encircles the larger inflatable member and the smaller cannula 44. The resulting effect is a cone-shaped chute 42 having walls of polymeric webbing.

The polymeric webbing, however, generally lacks the requisite rigidity to independently provide support for the inflatable member; the webbing is strong, but flaccid. The webbing merely aids in connecting the inflatable member to cannula 44. Advantages arise, however, from having such weak walls. In particular, the cannula 44 of pulling biliary catheter 40 and the inflatable member need not necessarily be in perfect alignment with one another. The polymeric webbing provides increased flexibility resulting in greater versatility in use. For example, the inflatable member may remain in perfect alignment behind the orifice of the papilla of Vater 22, while the remaining portions of pulling biliary catheter 40 may be at an offset angle to the orifice. The webbing in the above-described case would be taut on one side of chute 42, and flaccid on the other side.

Radiopacity is generally added to chute 42 having an inflatable member. Using radiopaque markers is particularly useful on chutes 42 having a remotely positioned inflatable member. Since remotely positioned inflatable members can achieve alignments unique to the other portions of the pulling biliary catheter 40, it is particularly useful for a physician to know the exact location and alignment of chute 42. As described in detail above, radiopacity can be imparted to chute 42 using numerous techniques known in the art.

Refer now to FIG. 4, wherein a guide biliary catheter 30 is shown advanced only as far as necessary to insure that guide biliary catheter 30 cannot "backout" during an ERCP procedure. Minimal advancement of guide biliary catheter 30 is counterintuitive to traditional "push-pull" techniques for cannulation. The present technique, however, is believed to substantially reduce trauma to the sensitive papillary tissue of the papilla of Vater 22.

Traditional pushing techniques require a biliary catheter to enter the sensitive papilla of Vater 22 and advance through the same to the appropriate pancreatico-biliary duct to be explored and treated. While the biliary catheter is being advanced, the outer wall of the biliary catheter slides across the sensitive tissue of the papilla of Vater 22. The combination of forward pressure and abrasion in this pushing technique increases trauma and inflammation to the surrounding papillary tissue.

Advancement of guide biliary catheter 30, on the other hand, is not for obtaining a treatment site deep within the pancreatico-biliary ducts. Guide biliary catheter 30 is only advanced as far as necessary to breach the sensitive tissue surrounding the orifice of the papilla of Vater 22. As will be discussed with respect to FIGS. 5 and 6, subsequent medical devices are then advanced within guide biliary catheter 30 to explore and treat the pancreatico-biliary ducts. These medical devices pass within guide biliary catheter 30 and emerge on the other side of the sensitive tissue, thereby refraining from contacting the sensitive papillary tissue. The subsequent medical devices, therefore, can be advanced and withdrawn without causing trauma and inflammation to the surrounding sensitive papillary tissue. In effect, guide biliary catheter 30 of the present invention eliminates the harmful effects of the traditional "pushing" technique for cannulation.

A guidewire (not shown) may be used in conjunction with guide biliary catheter 30 to facilitate accessing the orifice of the papilla of Vater 22. The guidewire is inserted through a lumen at the proximal end of guide biliary catheter 30 and guided through the catheter until it emerges from the distal end 32. A physician then threads the thin guidewire through the narrow orifice of the papilla of Vater 22. After the guidewire has entered the orifice, the guide biliary catheter is gently advanced over the guidewire. Any difficulty in breaching the orifice with guide biliary catheter 30 is generally resolved using the tapered distal tip 32, as previously described.

FIG. 5 illustrates the introduction of pulling biliary catheter 40 within the orifice of the papilla of Vater 22, and the initial deployment of the catheter's chute 42. Pulling biliary catheter 40 is inserted through a lumen at the proximal end of guide biliary catheter 30 once guide biliary catheter 30 is correctly positioned within the orifice of the papilla of Vater 22. The pulling biliary catheter 40 is then guided through guide biliary catheter 30 until it emerges from the distal end 32 of the catheter.

On occasion, anatomical positioning of the papilla of Vater 22 prevents access to either the common bile duct 26 or the pancreatic duct 28. Specifically, access is denied when the orifice of the papilla of Vater 22 is positioned against the contralateral wall 25, or septum, separating the pancreatico-biliary ducts.

The present invention modifies the "pull" technique for cannulation by using a biliary catheter that does not pull on the outside tissue of the papilla of Vater 22, but rather pulls from within the papilla of Vater 22. In a preferred embodiment of the present invention, a pulling biliary catheter 40 deploys a cone-shaped chute 42 within the orifice of the papilla of Vater 22.

Deployment of chute 42 depends upon the chute's particular configuration. If a self-expanding chute is utilized, a sleeve or sheath may need to be retracted in order to deploy chute 42 within the orifice of the papilla of Vater 22. Likewise, a self-expanding chute may be immediately deployed following the chute's emergence from the distal tip 32 of guide biliary catheter 30. A chute 42 using an inflatable member, on the other hand, needs to be inflated by positive pressure in order to expand within the orifice. Regardless of the deployment method, a deployed chute possesses a circumferential diameter greater than the orifice of the papilla of Vater 22.

FIG. 6 illustrates the withdrawal of the papilla of Vater 22 from the contralateral wall 25 using the deployed chute 42 of pulling biliary catheter 40. When chute 42 is deployed, the conical shaped chute acts as a wedge. The distal most end of chute 42 expands radially and outwardly, separating the orifice of the papilla of Vater 22 from the contralateral wall 25. Because the circumferential diameter of the deployed chute 42 is greater than the orifice of the papilla of Vater 22, when pulled upon, chute 42 cannot slide back through the orifice. Thus, when a physician gently pulls back upon pulling biliary catheter 40, chute 42 gently moves any papillary tissue away from the contralateral wall 25 or septum, thereby further cannulating the papilla of Vater 22. This pulling method results in significantly less trauma and irritation than conventional pulling techniques involving a sphincterotome.

FIG. 6 further illustrates the ease in introduction of additional medical devices into the appropriate duct when the papilla of Vater 22 is withdrawn from the contralateral wall 25. Guidewire 50 is shown inserted through the opening of chute 42 and into the appropriate duct of the biliary tree. Once guidewire 50 is properly positioned within the correct duct, a therapeutic biliary catheter (not shown) is advanced over guidewire 50. Similar to the above-described biliary catheters, the therapeutic biliary catheter comprises a proximal end, a distal end, and a cannula having at least one lumen running the length therebetween. The proximal end of the therapeutic biliary catheter possesses a hub assembly that permits the therapeutic biliary catheter to attach to the pulling biliary catheter, the guide biliary catheter or an endoscope, as well as permitting additional medical devices to attach thereto.

The cannula of the therapeutic biliary catheter is generally smaller and longer than that of pulling biliary catheter 40. This size difference permits the therapeutic biliary catheter to be inserted within a lumen of pulling biliary catheter 40. Likewise, since the therapeutic biliary catheter must be advanced farther into a patient's body during an ERCP procedure, the therapeutic biliary catheter is generally longer than pulling biliary catheter 40 or guide biliary catheter 30.

Therapeutic biliary catheters are ultimately the medical devices that treat the maladies requiring the ERCP procedure. Therapeutic biliary catheters are designed to explore and treat areas of blockage within the bile ducts by gallstones, tumors, scarring or other conditions that cause obstruction or narrowing (stricture) of the ducts. Similarly, blockage of the pancreatic ducts from stones, tumors, or stricture can also be evaluated and treated by a therapeutic biliary catheter, which is useful in assessing causes of pancreatitis (inflammation of the pancreas).

The medical devices are retracted from the patient in a reverse order after successfully treating the maladies requiring the ERCP procedure. The retraction of chute 42, in particular, generally corresponds to the chute's method of deployment. For example, if a sleeve or sheath were used to expand chute 42, then the same sleeve or sheath would be advanced over chute 42 in order to collapse the chute. After chute 42 is confined, the entire pulling biliary catheter 40 could be withdrawn from the endoscopic system. Similarly, if chute 42 were inflated, a physician would simply deflate chute 42 and retract pulling biliary catheter 40.

Figure 11:
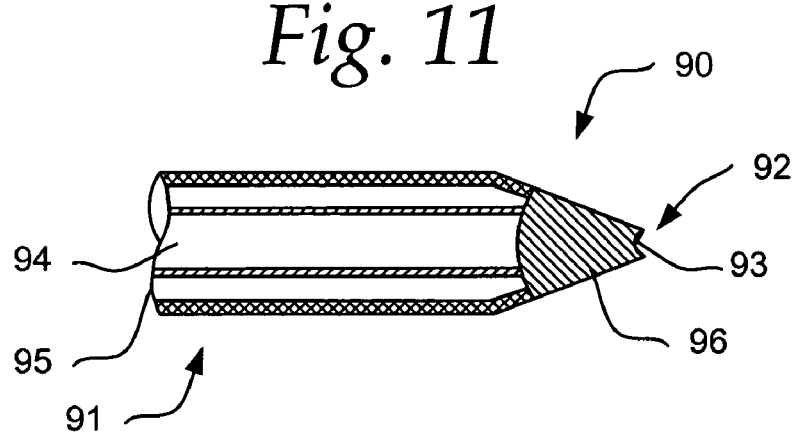
FIG. 11 is a partial cross-sectional view of the distal portion of a biliary catheter having a tapered distal end and an inflatable balloon disposed on the tapered distal end.
Figure 12:
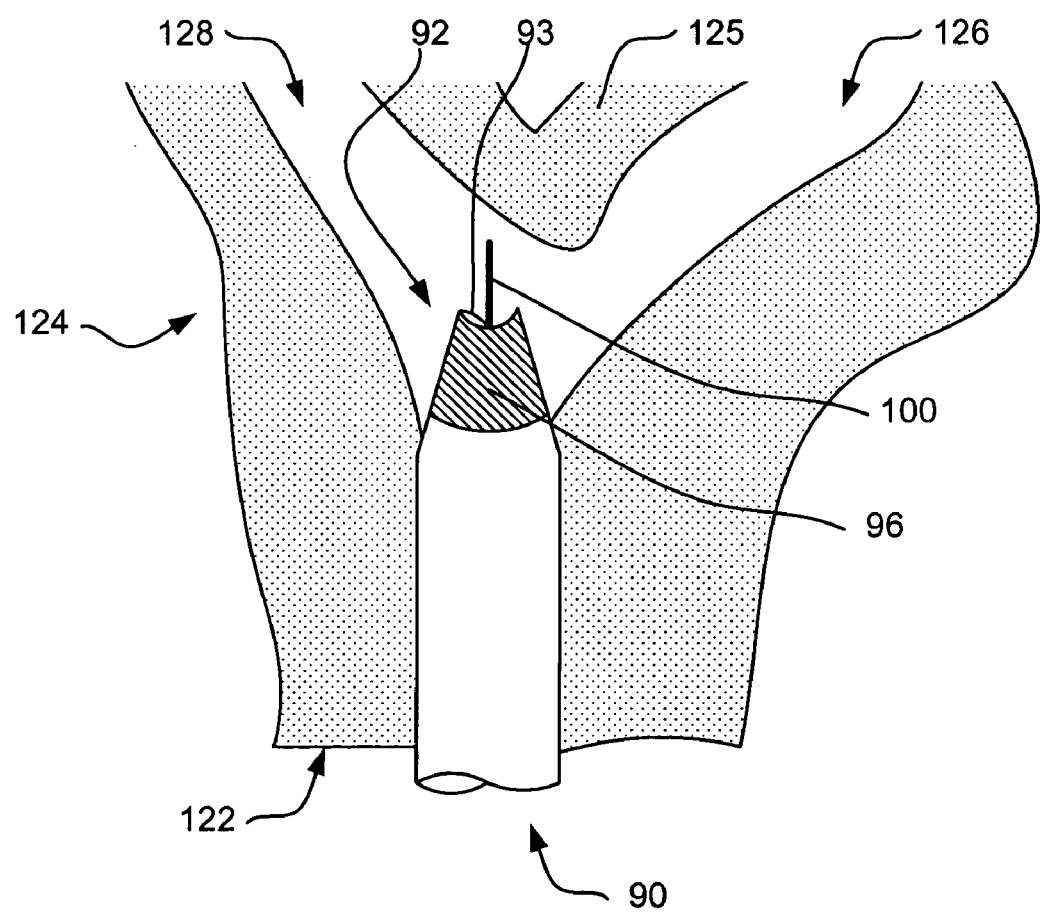
FIG. 12 illustrates the introduction of the biliary catheter of FIG. 11 within the orifice of the papilla of Vater.
Figure 13:
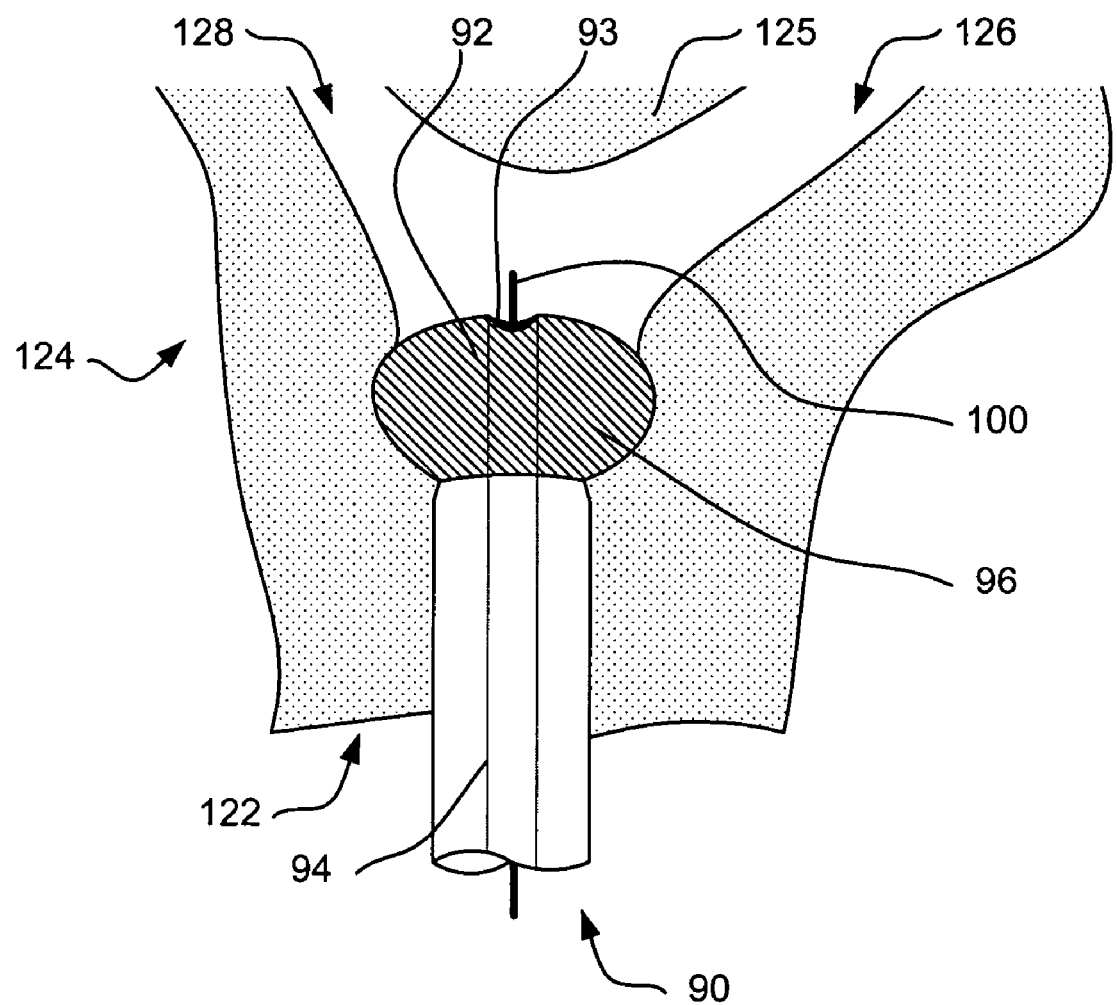
FIG. 13 illustrates the pulling back of the papilla of Vater from the contralateral wall using the inflated balloon of the biliary catheter of FIG. 12.

FIGS. 11-13 show alternative embodiments of the present invention. FIG. 11 shows a distal portion of an alternative biliary catheter 90. The biliary catheter 90 has a generally cylindrical proximal portion 91 and a tapered distal end 92, which may terminate in a distal tip. There may be one or more openings 93 in the distal end 92. Openings 93 in the distal tip may include various known devices and features to prevent fluid backflow through a lumen in fluid communication with such openings. The opening 93 shown is exaggerated in size for purposes of illustration.

A balloon 96 is attached to the tapered distal end 92. The balloon 96 may be designed to wrap around the distal end 92 in an unused or uninflated manner to minimally increase the diameter of the distal end 92. The balloon is in fluid communication with an inflation lumen 95 which extends to the proximal end of the biliary catheter 90. When inflated, the balloon 96 may assume a generally toroidal or donut shape. Other shapes, such as angular or semi-spherical shapes or discs, are also contemplated. In some embodiments, the biliary catheter 90 may be a zero-tip catheter, while in others the balloon catheter may incorporate a balloon set back from the distal tip by some distance.

The illustrative biliary catheter 90 shown in FIG. 11 is a zero-tip balloon catheter, but as noted, balloon arrangements are contemplated. Biliary catheter 90 includes two lumens 94, 95 in a coaxial alignment. Other multi-lumen side-by side or coaxial lumens are also contemplated, and in some embodiments, a single lumen catheter may also be used. In the illustrative embodiment shown in FIG. 11, the balloon 96 may be in fluid communication with one lumen, for example, outer lumen 95, in order that, once so desired, the balloon 96 may be inflated by applying positive pressure to a fluid at a proximal end of the outer lumen 95. If outer lumen 95 is in fluid communication with balloon 96, inner lumen 94 may be utilized as a guidewire lumen during insertion of the catheter 90, though a separate guidewire lumen may also be included (not shown). Also, inner lumen 94 could be used for advancement of other medical devices into a desired area.

In the multi-lumen catheter 90 incorporating a balloon 96, as shown in FIG. 11, one lumen 95 may be in fluid communication with the balloon 96, while the other lumen 94 is not. The lumen 94 not in fluid communication with the balloon 96 may or may not extend the entire length through the catheter 90; it may have a proximal end terminate in an opening anywhere along the length of the catheter 90, including a location proximal the distal end 92 or a location at the proximal end, or anywhere therebetween. In several embodiments, lumen 94 does have a distal end at an opening 93 in the distal tip of the balloon catheter. The lumen 94 may be used to pass guidewires as well as therapeutic biliary catheters from a proximal side to a distal side of balloon 96.

In some embodiments, a biliary catheter as shown in FIG. 11 could be used in fashion similar to that discussed above with respect to FIGS. 5 and 6, as a substitute for pulling biliary catheter 40 (shown in FIGS. 2 and 3). In such embodiments, biliary catheter 90 could be advanced inside a guide biliary catheter 30.

Alternatively, and as shown in FIG. 13, several embodiments use a biliary catheter 90 having at least one inner lumen 94 that maintains sufficient diameter or flexibility when the balloon 96 is inflated to enable one or more devices to be advanced distal the distal end 92 of biliary catheter 90, and a separate guide biliary catheter 30 is not necessary.

FIG. 12 shows biliary catheter 90 advanced into the papilla of Vater 122 in the biliary tree 124. The biliary catheter 90 may be advanced over guidewire 100, as shown, though guidewire 100 may not be necessary in some cases and biliary catheter 90 may be independently advanced into the papilla of Vater 122. Biliary catheter 90 may be advanced far enough to breach the tissue surrounding the orifice of the papilla of Vater 122. When positioned in this manner, the biliary catheter 90 may reduce potential irritation of papilla of Vater 122 if other devices are passed through biliary catheter 90.

On occasion, positioning of the papilla of Vater 122 prevents access to either the common bile duct 126 or the pancreatic duct 128. Specifically, access may be denied when the orifice of the papilla of Vater 122 is positioned against the contralateral wall 125, or septum, separating the pancreaticobiliary ducts.

FIG. 13 shows biliary catheter 90 where balloon 96 has been inflated. Balloon 96 is inflated to a diameter that is greater than the diameter of the orifice of the papilla of Vater 122. This may or may not require the balloon to be inflated to a maximum pressure allowable; in some embodiments, as shown in FIG. 13, the balloon 96 may be inflated to a pressure that is low enough to allow the balloon to deform to avoid irritating the papilla of Vater 122. When, as shown, biliary catheter 90 is pulled with balloon 96 inflated, the distal tip of biliary catheter 90 is pulled away from the contralateral wall 125. As the distal tip of the biliary catheter 90 is pulled away, the orifice of the papilla of Vater 122 is pulled away from contralateral wall 125, enabling access to either the common bile duct 126 or the pancreatic duct 128 via one or more openings 93 in the distal end 92 of biliary catheter 90.

In order to facilitate operable access to opening 93 distal of the distal end 92 of biliary catheter 90, one or more lumens may be included having rigid outer diameters and passing through the distal end 92 to the opening 93 on the distal tip. Alternatively, the balloon 96 may be designed to maintain an inner diameter sufficient for operable access. Operable access includes an opening sufficiently large to pass desired medical devices and wires. Such access need not be purely open access, but may instead be sufficient where a portion of a lumen 94 is compressed and closed off with a pressure weak enough to enable a device to be advanced through the lumen 94 against inward pressure. Thus, in some embodiments, the pressure of the inflated balloon 96 may be sufficient to prevent fluid backflow through an inner lumen 94, but may be low enough to allow passage of medical devices therethrough.

FIG. 13 also shows a lumen 94 having approximately consistent diameter passing from a location proximate the balloon 96 to the distal end 92 of the biliary catheter 90. Guidewire 100 may be advanced into common bile duct 126 or pancreatic duct 128. In several embodiments, a first guidewire may be used during advancement of the biliary catheter 90, and removed and replaced by a second guidewire after the biliary catheter 90 has reached a chosen position, or after balloon 96 has been inflated. Other medical devices may thus be advanced through lumen 94 over guidewire 100, regardless whether guidewire 100 was used during insertion of the biliary catheter 90, no guidewire was used during insertion of the biliary catheter 90, or guidewire 100 has been inserted after a guidewire used during insertion of biliary catheter 90 has been removed.

In some embodiments, a balloon 96 may be inflated to a first pressure to pull back the orifice of the papilla of Vater 122, and subsequently deflated to a second pressure to allow passage of devices through lumen 94. Such embodiments may prove useful in cases in which the papilla of Vater 122 is initially adjacent or near contralateral wall 125, but, once pulled away, papilla of Vater 122 does not forcibly return to a position adjacent contralateral wall 125.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is of course defined in the language in which the appended claims are expressed.

What is claimed is:

1. A method for gaining access to the ducts of the biliary tree via the alimentary canal, the method comprising the steps of:
    providing an endoscope having a working channel defined therein;
    advancing the endoscope through the alimentary canal of a patient to a position adjacent the papilla of Vater;
    providing a guiding biliary catheter having a lumen defined therein, a proximal end region, and a distal end region;
    advancing the guiding biliary catheter through the working channel of the endoscope and out from the working channel to a position adjacent an opening of the papilla of Vater;
    providing a pulling biliary catheter having a lumen defined therein, a proximal end, a distal end region, and an expandable chute extending distally from the distal end region of the pulling biliary catheter and forming a truncated cone, wherein the expandable chute includes an open distal end configured to expand radially such that an innermost extent of the open distal end is larger than an outermost extent of the distal end region of the pulling biliary catheter;
    advancing the pulling biliary catheter through the lumen of the guiding biliary catheter and into the opening of the papilla of Vater; and
    expanding the expandable chute of the pulling biliary catheter within the papilla of Vater.

2. The method of claim 1, further comprising the step of partially retracting the expanded chute of the pulling catheter.

3. The method of claim 2, wherein the step of partially retracting the expanded chute of the pulling catheter wedges the chute against the papilla of Vater.

4. The method of claim 3, wherein wedging the chute against the papilla of Vater separates the papilla of Vater from a contralateral wall in the biliary tree.

5. The method of claim 1, further comprising the step of advancing a guidewire through the pulling catheter to a duct within the biliary tree.

6. The method of claim 1, further comprising the step of advancing a therapeutic catheter through the pulling catheter to a duct within the biliary tree.

7. The method of claim 1, wherein the expandable chute is inflatable, and wherein the step of expanding the expandable chute of the pulling biliary catheter within the papilla of Vater includes inflating the chute.

8. The method of claim 1, wherein the distal end region of the guiding catheter is tapered.

9. The method of claim 1, wherein the endoscope includes a side port in communication with the working channel, and wherein the step of advancing the guiding catheter through the working channel of the endoscope and out from working channel to an opening of the papilla of Vater includes advancing the guiding catheter out from the side port.

10. The method of claim 1, wherein the chute includes one or more struts.

11. The method of claim 1, wherein the chute is self-expanding.

12. A method for gaining access to the ducts of the biliary tree, the method comprising the steps of:
    providing a first biliary catheter having a lumen defined therein, a proximal end region, and a distal end region;
    providing a second biliary catheter having a lumen defined therein, a proximal end, a distal end region, and an expandable chute having an open distal end and a proximal end disposed upon the distal end region of the second biliary catheter, wherein the open distal end is configured to expand radially outward away from the distal end region to an outermost extent larger than an outermost extent of the proximal end of the expandable chute;
    advancing the first biliary catheter through the alimentary canal of a patient to a position adjacent the opening of the papilla of Vater;
    advancing the second biliary catheter through the lumen of the first biliary catheter and into the opening of the papilla of Vater; and
    expanding the expandable chute of the second biliary catheter within the papilla of Vater.

13. The method of claim 12, further comprising the step of partially retracting the expanded chute of the second biliary catheter to improve access to the biliary tree.

14. The method of claim 13, wherein the step of partially retracting the expanded chute of the second biliary catheter wedges the chute against the papilla of Vater.

15. The method of claim 14, wherein wedging the chute against the papilla of Vater separates the papilla of Vater from a contralateral wall in the biliary tree.

16. The method of claim 12, further comprising the step of advancing a guidewire through the second biliary catheter to a duct within the biliary tree.

17. The method of claim 12, further comprising the step of advancing a therapeutic catheter through the second biliary catheter to a duct within the biliary tree.

18. The method of claim 12, wherein the step of advancing the first biliary catheter through the alimentary canal of a patient to a position adjacent the opening of the papilla of Vater includes advancing the first biliary catheter through an endoscope disposed in the alimentary canal.

19. The method of claim 12, wherein the expandable chute is inflatable, and wherein the step of expanding the expandable chute of the second biliary catheter within the papilla of Vater includes inflating the chute.

20. The method of claim 12, wherein the distal end region of the first biliary catheter is tapered.

21. A method for gaining access to the ducts of the biliary tree, the method comprising the steps of:
    providing a guiding biliary catheter having a proximal end, a distal end and a lumen extending the length therethrough, the guiding biliary catheter further having a tapered distal tip;
    providing a pulling biliary catheter having a proximal end, a distal end and at least one lumen extending the length therethrough, the pulling biliary catheter further having an expandable chute extending distally from the distal end of the pulling biliary catheter, wherein the expandable chute includes an open distal end configured to expand radially to a size larger than an outermost extent of the guiding biliary catheter;

providing a therapeutic biliary catheter;

advancing the tapered distal tip of the guiding biliary catheter within the opening of the papilla of Vater;

advancing the pulling biliary catheter through the lumen of the guiding biliary catheter and into the opening of the papilla of Vater;

expanding the expandable chute of the pulling biliary catheter within the papilla of Vater;

partially retracting the expanded chute of the pulling biliary catheter and pulling the papilla of Vater away from a contralateral wall separating the ducts of the biliary tree to improve access to the biliary tree; and advancing the therapeutic biliary catheter through the pulling biliary catheter and the open distal end of the expandable chute to the desired duct within the biliary tree.

22. A method for gaining access to the ducts of the biliary tree, the method comprising the steps of:

providing a biliary catheter having a proximal end, a distal end, a lumen extending the length therethrough and terminating in an opening in the distal end, and an inflatable balloon disposed proximate the distal end thereof;

advancing the biliary catheter into the opening of the papilla of Vater such that the balloon is disposed within the opening of the papilla of Vater;

inflating the balloon within the opening of the papilla of Vater;

partially retracting the inflated balloon to improve access to the biliary tree; and advancing a therapeutic catheter through the lumen beyond the distal end of the biliary catheter.

23. A method for gaining access to the ducts of the biliary tree, the method comprising the steps of:

providing a guiding biliary catheter having a proximal end, a distal tip and a lumen extending therethrough;

providing a pulling biliary catheter having a proximal end, a distal end and at least one lumen extending therethrough, the pulling biliary catheter further having an expandable chute extending distally from the distal end of the pulling biliary catheter, wherein the expandable chute includes an open distal end configured to expand radially to a size larger than an outermost extent of the guiding biliary catheter;

providing a therapeutic biliary catheter;

advancing the distal tip of the guiding biliary catheter within the opening of the papilla of Vater;

advancing the pulling biliary catheter through the lumen of the guiding biliary catheter and into the papilla of Vater;

expanding the expandable chute of the pulling biliary catheter within the papilla of Vater;

applying a force to an interior of the papilla of Vater in an antegrade direction using the expanded chute to improve access to the biliary tree; and advancing the therapeutic biliary catheter through the pulling biliary catheter and the open distal end of the expandable chute to the desired duct within the biliary tree.

* * * * *